(12) United States Patent
Tenerz et al.

(10) Patent No.: US 6,167,763 B1
(45) Date of Patent: Jan. 2, 2001

(54) PRESSURE SENSOR AND GUIDE WIRE ASSEMBLY FOR BIOLOGICAL PRESSURE MEASUREMENTS

(75) Inventors: Lars Tenerz, Uppsala; Ola Hammarström, Alunda; Leif Smith, Uppsala, all of (SE)

(73) Assignee: Radi Medical Systems AB, Uppsala (SE)

(*) Notice: Under 35 U.S.C. 154(b), the term of this patent shall be extended for 0 days.

(21) Appl. No.: 09/547,733

(22) Filed: Apr. 12, 2000

Related U.S. Application Data

(63) Continuation of application No. 08/952,825, filed as application No. PCT/SE96/00798 on Jun. 18, 1996.

(30) Foreign Application Priority Data

Jun. 22, 1995 (SE) .................................................. 9502303
Jan. 30, 1996 (SE) .................................................. 9600333

(51) Int. Cl.[7] ...................................................... G01L 7/00
(52) U.S. Cl. .............................................................. 73/756
(58) Field of Search ............................ 73/706, 719, 756; 128/637, 642, 667, 675, 673, 662.06

(56) References Cited

U.S. PATENT DOCUMENTS

| Re. 35,648 | 11/1997 | Tenerz et al. | 128/673 |
|---|---|---|---|
| 4,712,566 | 12/1987 | Hoek et al. | 128/748 |
| 4,941,473 | 7/1990 | Tenerz et al. | 128/637 |
| 4,957,110 | 9/1990 | Vogel et al. | 128/642 |
| 4,967,753 | 11/1990 | Haase et al. | 128/662.06 |
| 5,018,529 | 5/1991 | Tenerz et al. | 128/667 |
| 5,085,223 | 2/1992 | Lars et al. | 128/675 |
| 5,113,868 | 5/1992 | Wise et al. | 128/675 |
| 5,125,058 | 6/1992 | Tenerz et al. | 385/66 |
| 5,226,423 | 7/1993 | Tenerz et al. | 128/673 |

FOREIGN PATENT DOCUMENTS

| 0 387 453 A1 | 9/1990 | (EP) . |
| 96 00334 | 1/1996 | (SE) . |

OTHER PUBLICATIONS

Simultaneous Measurement of Flow Velocity and Trans–stenotic Pressure Gradient, (1994) (No month).
Textbook "Interventional Cardiology" 2nd Ed. W.B. Saunders Company (No date).
Dow Corning 360 Medical Fluid, Descriptive Literature available at least as early as 1997 (No date).

*Primary Examiner*—William Oen
(74) *Attorney, Agent, or Firm*—Foley & Lardner

(57) ABSTRACT

The invention relates to a sensor/guide wire device for biological pressure measurements having a guide wire (16, 17, 18, 21, 23) having a distal and a proximal end, and a pressure sensor device (19) mounted at the distal end of the guide wire. The distal portion can be a solid wire member (16) surrounded by a spiral member (18), and the sensor (19) can be an electrical sensor of a piezoresistive type. The sensor (19) is mounted on the solid wire (16). The sensor is mounted in a cantilevering fashion such that a pressure sensitive end of the sensor does not contact any structure other than its mount. This prevents forces (bending artifacts) from being exerted on the sensor, which could otherwise interfere with pressure measurements.

20 Claims, 8 Drawing Sheets

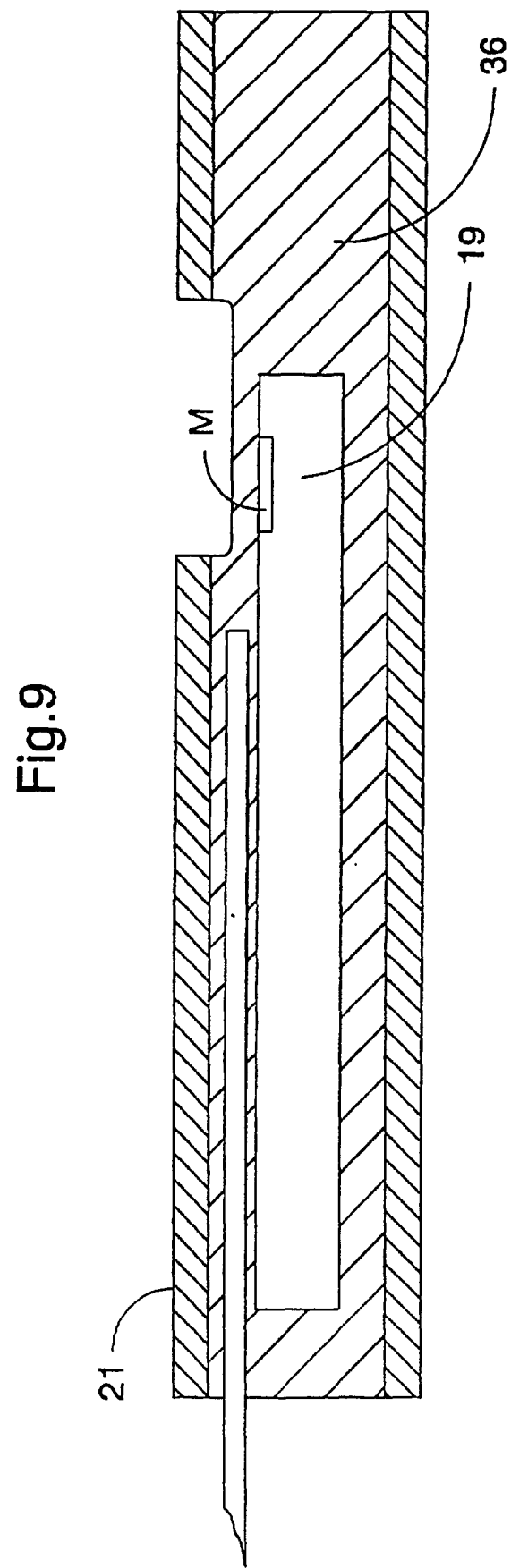

PRESSURE SENSOR AND GUIDE WIRE ASSEMBLY FOR BIOLOGICAL PRESSURE MEASUREMENTS

This application is a continuation of U.S. application Ser. No. 08/952,825 (filed Dec. 4, 1997), which is the National Stage of PCT application PCT/SE96/00798, filed Jun. 18, 1996.

The present invention relates to pressure measurements inside a living body, and in particular to a sensor/guide device having a guide wire and a distal sensor for pressure measurements in stenotic vessels of atherosclerotic vessels.

In a particular aspect the present invention relates to a sensor arrangement for minimizing bending artifacts, such as those referred to as catheter-whip, in a sensor/guide device.

For the purposes of this patent specification the term "guide wire" means a device for guiding and placing e.g. catheters in vessels in a living body.

The term "fluid" means gaseous, such as air, nitrogen, noble gases, etc, or liquid, such as blood, other body fluids, water, silicone oil, etc.

The term "cantilevering" means that one end of a structure is rigidly mounted, and the opposite end of the structure protrudes from the site of mounting into a medium that is substantially less rigid than that at the mounting site.

The term "rigidly mounted" means that mechanical stress in the structure to which an element is mounted will be carried over to the element at the point of attachment.

BACKGROUND OF THE INVENTION

Devices of the above identified type are known from e.g. Swedish Patents SE-85 00104-8, 86 02836-2, 86 03304-0, 88 02765-1, 90 02415-9, and European Publication EP-0 387 453.

All of these prior devices have a differential type pressure transducer/sensor, i.e. the pressure is measured as a differential between the applied pressure and atmospheric pressure. Such systems require a ventilation channel for levelling or equalizing the pressure difference between the backside of a pressure sensitive membrane and atmospheric pressure.

There are several advantages of a pressure measurement device for biological pressure measurements having. a differential type pressure transducing system, as opposed to an absolute measurement technique. First, the pressure value of interest is in fact a pressure differential between e.g. the pressure inside an organ and atmospheric pressure. Secondly, there is no need for compensation for atmospheric pressure fluctuations. Thirdly, it is advantageous to use an effective pressure measurement range of 0–300 mm Hg, rather than 760–1060 mm Hg, the latter prevailing when atmospheric pressure is part of the measured value. Fourthly, there is no vacuum required in the reference chamber, and the ventilation channel will equalize the pressure changes occurring in the reference cavity due to e.g. temperature fluctuations. Finally, it is possible to calibrate device by applying a negative pressure in the ventilation channel.

In Swedish Patent SE-86 03304-0 the ventilation channel is located inside thin tubes. This solution gives problems with the mechanical properties when the device is used as a guide wire, because the tubes are more easily deformed than solid wires.

In Swedish Patent SE-90 02416-7 another solution is disclosed having a solid core and an outer plastic tubing.

The devices of the prior art mentioned above suffer all from manufacturing problems in that the sensor elements can only be tested after substantial assembly work has been carried out.

However, despite all the advantages of the prior art devices of the differential pressure measurement type over absolute pressure measurements, there are some disadvantages too. The disadvantages become more pronounced when dimensions become smaller, and are mainly related to the presence of the ventilation channel.

For example, the flow resistance of the channel is a function of the limiting frequency response, and therefor the channel must have a certain cross section, i.e. there is a lower limit with respect to the usable dimensions.

A general problem with guide wire micro pressure transducers for in vivo measurements is the occurrence of bending artifacts when the sensor element is subjected to mechanical stress. One such artifact is referred to as catheter-whip, meaning a shift in the signal when the sensor element passes a sharp turn. A solution to such problems is to reinforce the region near the sensing element, so that this region becomes stiff. Such a solution is presented in SE-8603304-0, corresponding to U.S. Pat. No. 4,941,473.

However, the solution according to said patent requires that the sensing element allows a certain deformation/ deflection in relation to the bending resistance of the reinforced/-ing part and the surrounding proximal and distal portions, since the overall mechanical behaviour of the guide wire limits this relation. In the pressure sensor devices previously developed by the present applicants, primarily based on optical transducers, where the pressure signal is based on deflection of a silicon beam, the mentioned requirements are satisfactorily met, since the deflection is about 30 $\mu$m/300 mmHg. However, in sensors depending on smaller mechanical deflection, about 1 $\mu$m/300 mmHg or less, it is very difficult to achieve enough mechanical difference in the bending resistances between the reinforced portion and the surrounding, distal and proximal structure.

Conventional guide wires are commonly comprised of a long solid wire (e.g. 1.75 m) the distal portion (approx. 30 cm) having a reduced diameter to increase flexibility. Guide wires having sensors mounted at the tip on the other hand commonly require tubes for accommodating optical fibres and/or electrical leads to/from the sensors, and also for use as a ventilation channel as indicated above.

On the distal end of all types of guides there is normally provided a spiral or helix, in order to maintain the same diameter over the entire length of the guide. It also enables the distal wire portion inside the spiral or helix to be turned while the spiral remains at rest against the vessel wall or interior wall of a catheter.

It would be desirable to have a guide having the advantageous properties of a conventional type guide, and having an absolute pressure sensor integrated therewith. A prerequisite for this would be to provide an absolute pressure sensor/transducer, without need for a ventilation channel.

SUMMARY OF THE INVENTION

The inventors have now discovered that it is possible to make a sensor/guide device provided with an absolute pressure transducer, that still meets the same requirements as those of prior art differential pressure type devices, and in addition eliminates the bending artifact problems.

This is achieved according to the invention with a micro pressure sensor arrangement, by arranging the sensor element such that it protrudes in a cantilevering fashion, preferably without any contact with surrounding structures of the guide wire, and by a sensor/guide device incorporating such a sensor arrangement.

In a preferred embodiment, the sensor is an electrical sensor of piezoresistive type. A suitable sensor is disclosed in our Swedish patent application 9600334-8, filed Jan. 30, 1996.

In a still further embodiment the electrical cabling needed for connection to a recording apparatus is integrated in the distal portion of the guide wire.

Further scope of applicability of the present invention will become apparent from the detailed description given hereinafter. However, it should be understood that the detailed description and specific examples, while indicating preferred embodiments of the invention are given for illustration only, since various changes and modifications within the spirit and scope of the invention will become apparent to those skilled in the art from this detailed description.

The present invention will become more fully understood from the detailed description given herein below and the accompanying drawings which are given for illustration only, and thus are not limitative of the present invention.

BRIEF DESCRIPTION OF THE DRAWINGS

In the drawings

FIG. 9 shows a further embodiment of the sensor, wherein the pressure sensitive portion is embedded in e.g. silicone.

DETAILED DESCRIPTION OF THE INVENTION

Figure 1:
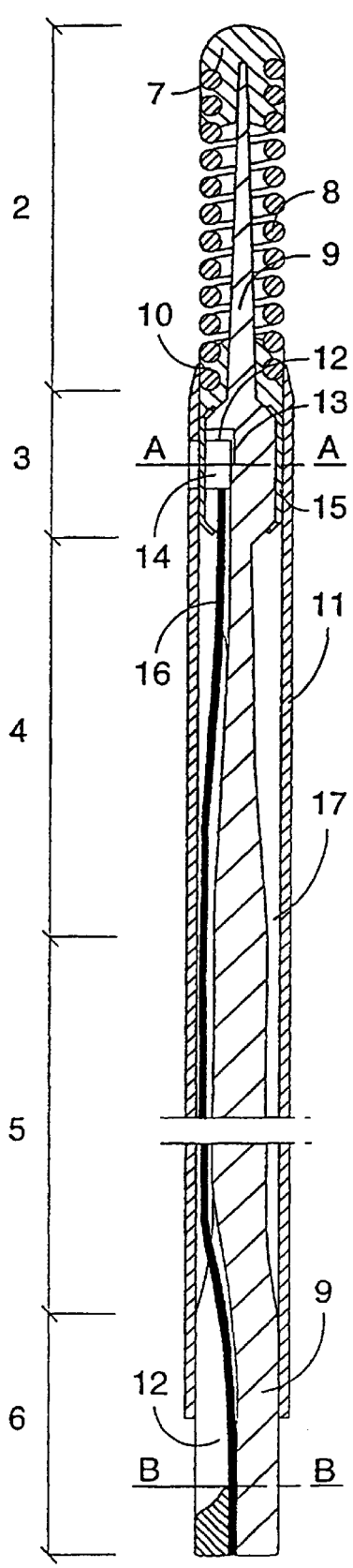
FIG. 1 shows a prior art sensor/guide wire construction having a differential pressure sensor, wherein the sensor element is in contact with a pressure transducing membrane.

With reference to FIG. 1 there is shown a prior art device (disclosed in SE-9002416-7).

The sensor/guide device 1 has in the drawing been divided into five sections, 2–6, for illustrative purposes. The section 2 is the most distal portion, i e that portion which is going to be inserted farthest into the vessel, and section 6 is the most proximal portion, i e that portion being situated closest to a (not shown) electronic unit. Section 2 is about 10–50 mm, section 3 about 1–5 mm, section 4 about 200–400 mm, section 5 about 1000–2000 mm and section 6 about 10–100 mm.

Section 2 comprises a radiopaque coil 8, being made of e g platinum, provided with an arced tip 7 being brazed or alternatively welded. In the platinum coil 8 and the tip 7 respectively, there is also attached stainless, solid metal wire 9 which in section 2 is formed like a thin conical tip and functions as a security thread for the platinum coil 8. The successive tapering of the metal wire 9 in section 2 towards the arced tip 7 results in that the front portion of the sensor guide construction becomes successively softer. The tapering is obtained by cylindrical grinding of the metal wire 9.

At the transition between the sections 2 and 3 the lower end of the coil 8 is attached in the wire 9 with glue or alternatively solder, forming a joint 10. At the joint 10 a thin outer tube 11 commences which is made of a biocompatible material, e g polyimid, and extends downwards in the figure all the way to section 6. The tube 11 has been treated to give the sensor guide construction a smooth outer surface with low friction. The metal wire 9 is heavily expanded in section 3, and this section is provided with a slot 12 in which a sensor element 14 is arranged, e g a pressure gauge. The expansion of the metal wire 9 in which the sensor element 14 is attached decreases the stress exerted on the sensor element in sharp vessel bends. Preferably a recess 13 is arranged in the slot 12, providing an extra deep area under the site of the pressure sensitive part of the sensor element 14 so that the sensor element will not experience any mechanical stress if the wire 9 is bent, i e the recess forms a clearance for the sensor element 14.

The recess 13 and the slot 12 are made by spark machining in the metal wire 9. The slot 12 has the approximative dimensions 100 $\mu$m width ×100 $\mu$m depth, whereby the length can be varied as desired. The sensor element is sealed against surrounding blood pressure with a hose 15 covering the expansion of the wire 9. The hose 15 functions as a soft membrane and is made of a flexible material. On the outside of the sensor element 14 and the hose 15 lying thereover an opening is arranged in the tube 11, so that the sensor element comes in contact with the environment in order to perform, for example, pressure measuring.

From the sensor element 14 there is arranged a signal transmitting cable 16 which can be an optic fibre or electric cables 16. The signal transmitting cable 16 extends from the sensor element 14 to a (not shown) electronic unit being situated below the section 6. The metal wire 9 is substantially thinner in the beginning of section 4 to obtain good flexibility of the front portion of the sensor guide construction.

This device records mechanical deflections of about 30 $\mu$m/300 mmHg of pressure. With deflections of this magnitude certain deformations of the sensing element occur due to bending of the guide wire. The reinforcement of a portion of the sensing element will not carry mechanical stress over to the distal end of the sensor, and thus will not influence the recorded pressure values significantly.

However, in arrangements where the deflection is of the order of 1 $\mu$m/300 mmHg, it is difficult if not impossible to achieve enough mechanical difference in the bending resistances of the stiff or rigid portion where the sensor is mounted, and the distal and proximal portions of the guide wire. If on the other hand the distal and proximal wire portions are too flexible the "pushability" of the guide wire as a whole will be inadequate. One has therefor to find a compromise between these extremes.

Figure 2:
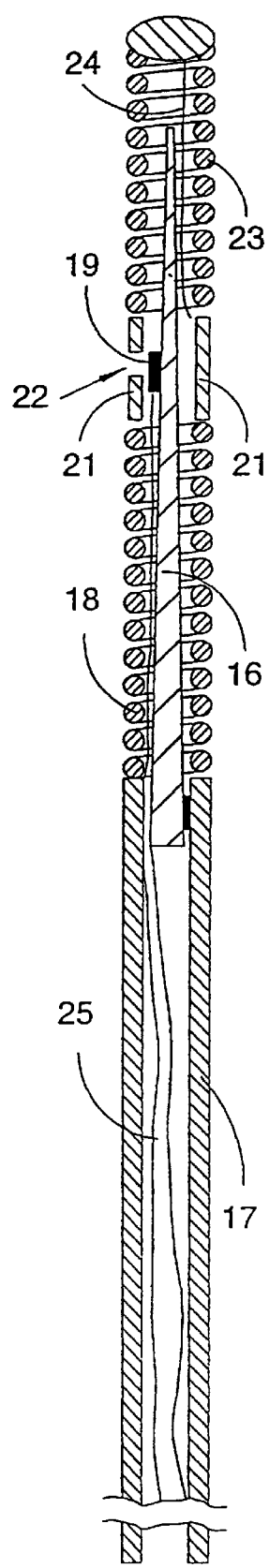
FIG. 2 shows a sensor/guide wire assembly in longitudinal cross section.

Now turning to FIG. 2 there is shown a sensor/guide device of the invention. Thus, the sensor/guide device comprises a solid wire 16 which is machined by so called centering grinding, and inserted into a proximal tube portion 17. The wire 16 forms the distal portion of the guide, and extends beyond the distal end of the proximal tube portion 17 where said tube is connected to or integrally formed with a spiral portion 18. On the distal end of the wire 16 there is mounted an absolute pressure sensor 19, such as the one disclosed in our copending Swedish patent application 9600334-8.

On the distal end of the wire 16 there is mounted a pressure sensor 19 provided with a pressure sensitive device comprising a membrane M of polysilicon and a piezoresistive element provided thereon. Between the wire 16 and the spiral portion 18, electrical leads 4 from the electronic circuitry run parallel with said wire 16.

It is important that the pressure sensitive membrane of such a sensor is mounted in the device in such a way that bending artifacts are minimized or eliminated. This may be achieved by ascertaining that there is no possibility for the chip edges to come into contact with the surrounding tube (see FIGS. 3–9), and there are several possible methods of mounting in accordance with the invention, described below.

The sensor 19 is protected by a short section of a tube 21 having an aperture 22 through which surrounding media act on the pressure sensor. At the very distal end of the entire device there is an X-ray non-transparent spiral 23, e.g. made of Pt, and used for location purposes, and a safety wire 24 for securing the distal part of the spiral 23.

Thus, by providing a solid wire the drawbacks of the prior art devices of the vulnerability to bending are in practice eliminated.

In one embodiment of the invention the wire 16 is made of stainless steel, which is conventional. Alternatively a so called shape memory metal can be used. This may be an advantage since memory metal is superelastic and will not deform as easily as other materials. To minimize the number of electrical leads, the wire may be used as one of the electrical leads.

The proximal tubing 17 and the spiral 18 may be coupled so as to be utilized as an electrical shield, in which case it of course cannot be used as an electrical lead.

An example of a pressure sensor arrangement suitable for use with the invention is described below.

Figure 3:
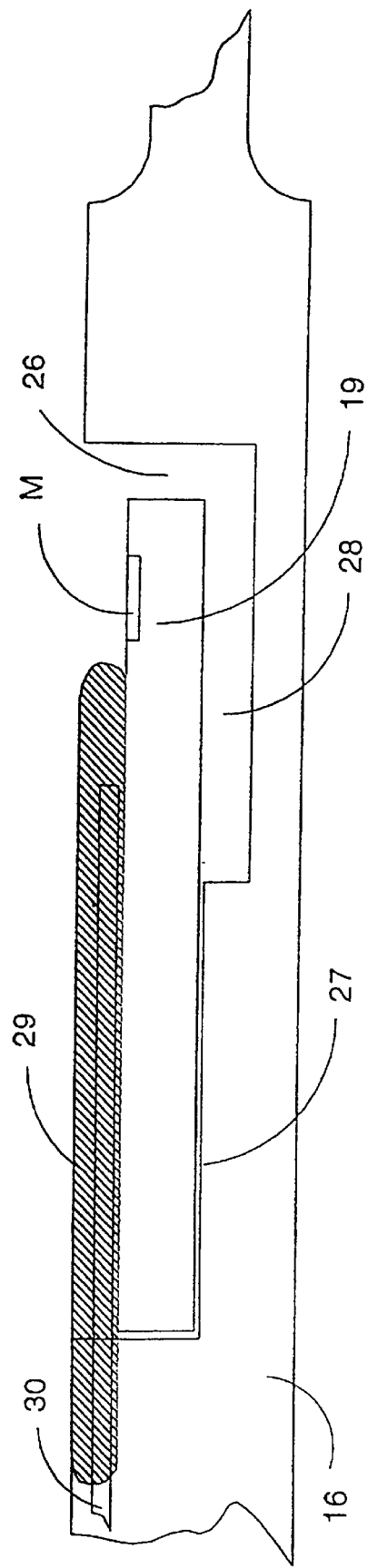
FIG. 3 shows a first embodiment of the sensor arrangement of the invention.

In still another embodiment the wire 16 has been machined e.g. by grinding, spark erosion or laser techniques to form a recess or groove 26 in which the sensor element is mounted in a cantilevering fashion (FIG. 3). Thus the entire mounting structure provides a free space surrounding the distal part of the chip 19, this free space allowing air or blood or other pressure exerting media to enter the interior and to act on the sensor, which in its turn delivers a signal representative of the exerted pressure.

The free space needed to accommodate the sensor when the assembly is subjected to bending may be defined as discussed below, and is best explained in relation to the embodiment shown in FIG. 7, although the same principal reasoning is valid for all embodiments. The minimum required distance in order that contact between sensor and surface 25 be avoided can be estimated as follows.

For a given stiffness the bending radius of the portion comprising the sensor element 19 is denoted R, and the length of the portion of the sensor protruding out from the mounting structure is denoted L. If we assume that these two distances form the small sides of a right angled triangle (see inset of FIG. 7), the right angle being located at 25 in FIG. 7, then the hypotenuse H is given by $$H = \sqrt{R^2 + L^2} \quad \text{(I)}$$

If we denote the gap between the bottom side of the sensor and the surface 25 with δ, the minimum gap needed for avoiding mechanical contact between the sensor and the surrounding solid structure during bending is approximately $$\delta = H - R \quad \text{(II)}$$

It is also possible and within the scope of the inventive idea to fill the space with e.g. silicone rubber to provide a protective medium around the chip. It is also conceivable to fill the space with a fluid. This requires high enough viscosity and surface tension (e.g. silicone oil) in order that such fluid will stay in place.

The groove 26 (FIG. 3) consists of two portions, a first having the purpose of a mounting shelf 27 for receiving the proximal part of the sensor chip. The second portion 28 is deeper than the first, in order to allow the distal part of the sensor chip to protrude freely even in a case where the wire tip is bent or deflected as discussed previously. Thus the entire recess 26 is made in a two-step fashion. In this embodiment one may refrain from providing a protective tubing. In such a case (i.e. no protective tubing), the chip needs to be positioned in such a way that the upper surface 29 of the chip is located slightly below the upper surface 30 of the wire 16, in order to avoid interference by the blood vessel walls. This embodiment is advantageous in that it makes mounting easier, and it saves space, since one avoids the outer tubing.

Figure 4:
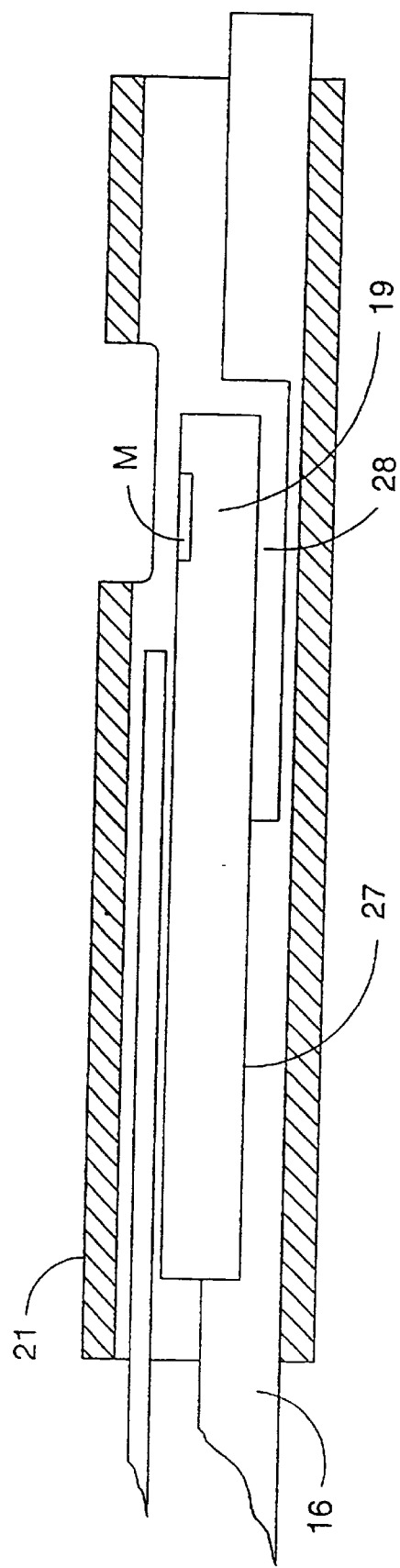
FIG. 4 shows a second embodiment of the sensor arrangement of the invention.

In accordance with another embodiment, shown in FIG. 4, a tube 21 is provided around the assembly comprising wire and chip, leaving an opening to expose the sensor chip against the surrounding medium the pressure of which is to be measured. The provision of a tube enhances the mechanical stability, and acts as a spacer means to provide further distance between the surroundings and the chip.

Figure 5:
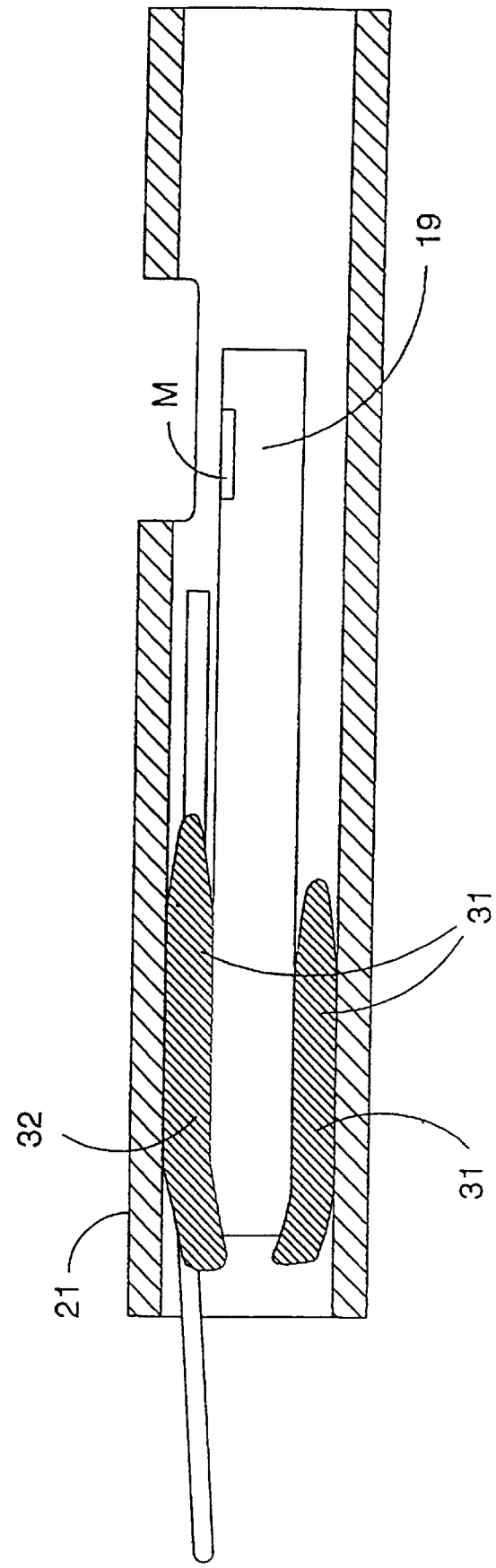
FIG. 5 shows a third embodiment of the sensor arrangement of the invention.
Figure 6:
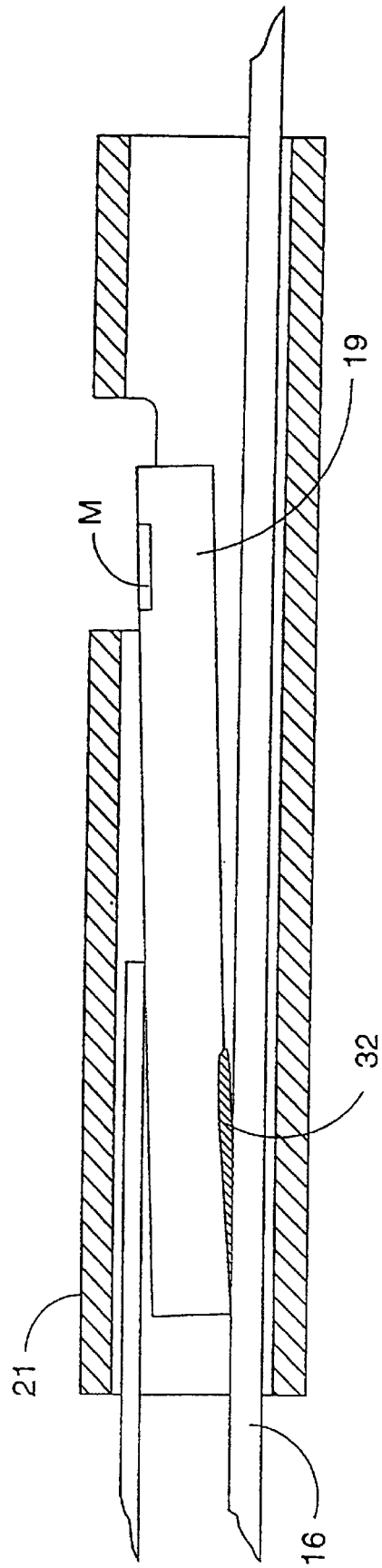
FIG. 6 shows a fourth embodiment of the sensor arrangement of the invention wherein the sensor element is mounted in an inclined position.

In FIG. 5 an embodiment is shown wherein no wire is used. The proximal end of the sensor chip 19 is shown as simply attached (glued) 31 against the inner wall of the tube, and on the opposite side there is a spacing between the chip and the inner wall of the tube. The point of attachment of the cabling is slightly elevated from the surface of the chip, because of the spot of glue 32 having a finite thickness.

It is also possible to mount the sensor element 19 by gluing 32 in an inclined position (FIG. 6) on a wire 16. In this case one may refrain from machining the wire to form a groove, as in the embodiment of FIG. 3. This has the advantage of being a simple method of mounting, and thus has economic benefits.

Figure 7:
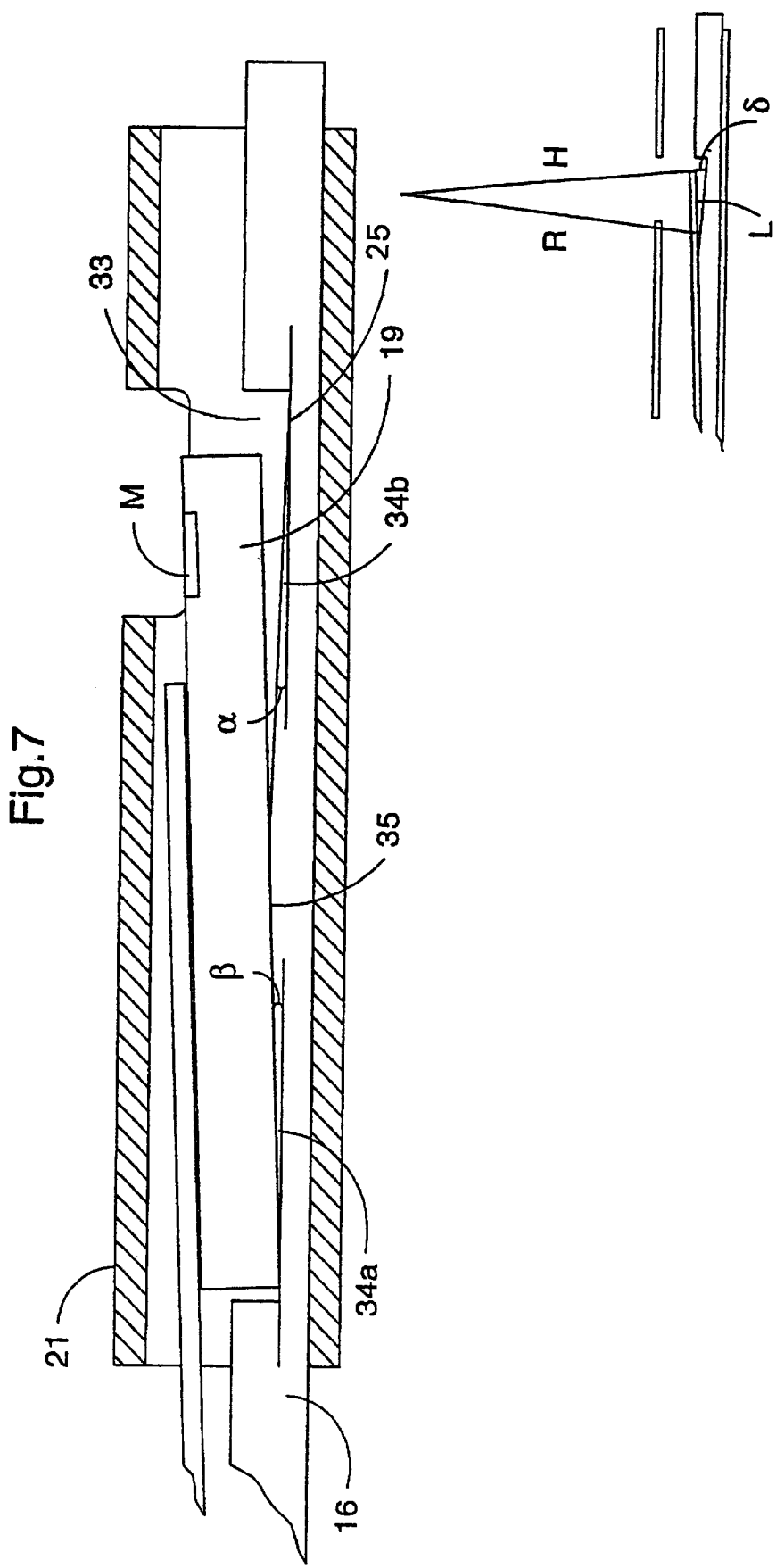
FIG. 7 shows a fifth embodiment of the sensor arrangement of the invention wherein the sensor element is mounted in an inclined position.

In a still further embodiment a groove 33 is made as shown in FIG. 7. In this case the recess or groove, having a bottom 34a, 34b with a slightly elevated centre 35, has been cut or machined in the solid wire to provide space for free movement of the protruding chip end through an angle. The angles, as shown in the Figure are approximately α=1–3° and β=1–3° in a preferred embodiment. The recess 33 is made by grinding, spark erosion or by laser machining, methods well known to the skilled individual. The space under the distal end of the sensor is of the order of 20–50 μm, but could be even smaller depending on the length of the protruding part of the sensor. This embodiment is particularly advantageous since the inclined position of the sensor element makes it is possible to make the outer diameter even smaller, thus further facilitating insertion in blood vessels.

Figure 8:
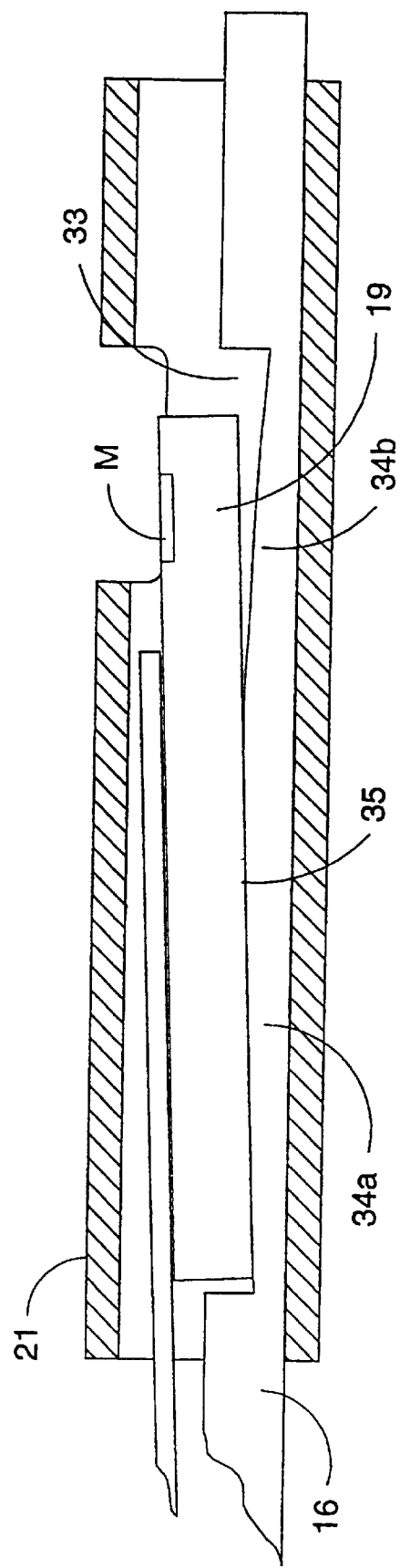
FIG. 8 shows a sixth embodiment of the sensor arrangement of the invention wherein the sensor element is mounted in an inclined position.

Still another embodiment is shown in FIG. 8. This is a variation of the embodiment of FIG. 8. Here the bottom 34a, 34b of the recess 33 is rounded which may be advantageous in that the chip might not so easily break. The edge 35 of the bottom profile in FIG. 7 could act as a cutting edge in certain circumstances. However, the rounded structure is more difficult and thus costlier to manufacture.

Still another embodiment, shown in FIG. 9, is contemplated within the spirit of the invention, namely that the entire sensor chip 19, be imbedded in a very soft, elastic medium 36 such as silicone rubber. This would protect the chip 19 entirely from mechanical impact by surrounding structures, and still would expose the membrane M to a medium having the ability to transfer/convey pressure changes, such that the membrane will detect such changes in the fluid passing in the vessel in which the sensor is situated. Also, an imbedded sensor would not be exposed to blood or other fluids, which potentially could cause short circuit in the electric circuits.

In a further embodiment of the device according to the present invention the sensor/guide device is provided with an additional sensor element, namely a flow sensor for measuring the blood flow in a vessel.

The background for this is that in certain pathological states, e.g. so called "small vessel disease" (capillary vessels in the heart muscle are malfunctioning), it is not sufficient to measure the pressure in said vessels. This is because in fact a perfectly normal pressure may be detected, but nevertheless there is a severe malfunction in that the vessel may be almost entirely blocked, and thus there is very little flow in said vessel. By providing an option to measure bloodflow, the physician may arrive at the correct diagnosis and prescribe treatment with appropriate medicines.

The flow can be measured either electrically or by using an ultrasonic technique.

The electrical technique is based on temperature changes incurred by the velocity of flow, cooling being a function of flow rate. More rapid flow yields a larger temperature drop.

The ultrasonic technique is based on transmitting an ultrasonic pulse from a crystal and detecting the doppler shift in the echo reflected from the blood cells. Such velocity sensors are available from Cardiometrics, Inc. Mountain View, Calif., USA.

The invention being thus described, it will be clear that the same may be varied in many ways. Such variations are not to be regarded as a departure from the spirit and scope of the invention and all such modifications as would be clear to one skilled in the art are intended to be included within the scope of the following claims.

We claim:

1. A guide wire for biological pressure measurements, comprising:
   a wire;
   a mount; and
   a pressure transducer for biological pressure measurements mounted to the wire via the mount such that a pressure sensitive end of the pressure transducer does not contact any structure other than the mount.

2. A guide wire as set forth in claim 1, wherein the pressure transducer is cantilevered from the mount.

3. A guide wire as set forth in claim 1, further comprising a tube surrounding at least a portion of the wire.

4. A guide wire as set forth in claim 1, further comprising at least one signal line running from the pressure transducer along the wire.

5. A guide wire as set forth in claim 1, wherein the pressure transducer is an absolute pressure sensor.

6. A guide wire as set forth in claim 1, wherein the wire includes shape memory material.

7. A guide wire as set forth in claim 1, wherein the wire serves as an electrical lead for the pressure transducer.

8. A guide wire as set forth in claim 1, further comprising a radiopaque tip.

9. A guide wire as set forth in claim 2, further comprising a tube, wherein a cantilevered portion of the pressure transducer and the tube define a free space around the cantilevered portion.

10. A guide wire for biological pressure measurements, comprising:
    a wire;
    a tube connected to the wire;
    a mount; and
    a pressure transducer for biological pressure measurements mounted to the wire via the mount such that a pressure sensitive end of the pressure transducer does not contact the tube or any structure other than the mount.

11. A guide wire as set forth in claim 1, further comprising a flow sensor.

12. A guide wire as set forth in claim 10, further comprising a flow sensor.

13. A guide wire as set forth in claim 1, further comprising a flexible coil.

14. A guide wire as set forth in claim 10, further comprising a flexible coil.

15. A guide wire as set forth in claim 1, wherein the pressure sensitive end is recessed from an outer periphery of the guide wire.

16. A guide wire as set forth in claim 10, wherein the pressure sensitive end is recessed from an outer periphery of the guide wire.

17. A guide wire as set forth in claim 1, wherein the pressure transducer is a piezoresistive pressure transducer.

18. A guide wire as set forth in claim 10, wherein the pressure transducer is a piezoresistive pressure transducer.

19. A guide wire as set forth in claim 1, wherein the pressure transducer has a sensitivity on the order of 1 $\mu$m/300 mm/Hg.

20. A guide wire as set forth in claim 10, wherein the pressure transducer has a sensitivity on the order of 1 $\mu$m/300 mm/Hg.

* * * * *